(12) United States Patent
Krueger et al.

(10) Patent No.: US 10,733,732 B2
(45) Date of Patent: Aug. 4, 2020

(54) METHOD FOR COMPARATIVE VISUALIZATION OF IMAGE ANALYSIS FEATURES OF TISSUE

(71) Applicant: Flagship Biosciences, Inc., Westminster, CO (US)

(72) Inventors: Joseph Krueger, Andover, MA (US); Allison S. Harney, Boulder, CO (US); Chris L. Luengo Hendriks, Broomfield, CO (US)

(73) Assignee: Flagship Biosciences, Inc., Westminster, CO (US)

( * ) Notice: Subject to any disclaimer, the term of this patent is extended or adjusted under 35 U.S.C. 154(b) by 72 days.

(21) Appl. No.: 16/050,907

(22) Filed: Jul. 31, 2018

(65) Prior Publication Data
US 2020/0043166 A1    Feb. 6, 2020

(51) Int. Cl.
  *G06T 7/00* (2017.01)
  *G01N 1/30* (2006.01)
  *G01N 33/53* (2006.01)
  *G06K 9/00* (2006.01)

(52) U.S. Cl.
  CPC ............. *G06T 7/0014* (2013.01); *G01N 1/30* (2013.01); *G01N 33/53* (2013.01); *C12Q 2600/118* (2013.01); *C12Q 2600/158* (2013.01); *G06K 9/00127* (2013.01); *G06T 2207/30024* (2013.01)

(58) Field of Classification Search
  CPC ....... G06T 7/0012; G06T 7/0014; G01N 1/30; G01N 33/53
  See application file for complete search history.

(56) References Cited

U.S. PATENT DOCUMENTS

| 9,304,068 B2 * | 4/2016 | Morimoto | G01N 1/286 |
| 2019/0286790 A1* | 9/2019 | Kaigala | G16H 50/30 |
| 2019/0294859 A1* | 9/2019 | Varekamp | G06K 9/00127 |

\* cited by examiner

*Primary Examiner* — Sam Bhattacharya
(74) *Attorney, Agent, or Firm* — Josiah Barbour

(57) ABSTRACT

In accordance with the embodiments herein, a method for displaying differences and similarities between tissue samples utilizing a reference database consisting of tissue images, image analysis features, and derived score from patient tissue samples assayed with a tissue-based test for the purpose of scoring said patient sample and guiding treatment based on said score. The method described herein utilizes digital image analysis of a tissue image of one or more tissue sections to extract features which generates a dataset mathematically representing the image. This dataset is then compared to the reference database to determine reference images with similar and different feature values. Those images are then displayed with the similar and different features highlighted.

9 Claims, 7 Drawing Sheets

Tissue section 1, with overlay that highlights relevant cells

Comparators from reference cohort

Tissue section 1, with overlay that highlights relevant features

Comparators from reference cohort

Tissue section 1, with overlay that highlights relevant features

Comparators from reference cohort

METHOD FOR COMPARATIVE VISUALIZATION OF IMAGE ANALYSIS FEATURES OF TISSUE

BACKGROUND

Field of the Invention

The present invention relates in general to image analysis methods for the assessment of histological and immunohistochemistry (IHC) assays applied to tissue. More specifically, the present invention relates to methods of enhancing a pathologist's ability to analyze tissue samples using a visual comparison of image analysis features.

Description of the Related Art

The majority of current tissue-based (e.g., IHC, immunofluorescent (IF), mass spectrometry imaging (MSI)) in vitro diagnostic assays, companion diagnostics, laboratory developed tests, and research use only assays are based on measuring 1) the expression level of a single biomarker within a patient's tissue specimen, or 2) assessing the frequency of biomarker-positive, or graded expression levels of, cells within a patient's tissue specimen. Scoring these attributes of the tissue and biomarker(s) using quantitative (e.g., image analysis), semi-quantitative (e.g., manual pathologist H-score), or qualitative (e.g., manual pathology 0, 1, 2, 3+ scoring paradigm) methods informs a physician's determination of diagnosis, prognosis, or to guide future treatment decisions.

However, tissue-based assays only evaluate biomarker positivity or expression levels in tissue with limited regard to the geographic distribution or pattern of cells. Some efforts have been made to evaluate simplistic relationships between multiple cell types within tissues. These assessments, however, are relatively simplistic assessments of cell distribution (e.g., biomarker positive cells in the tumor tissue compartment) or patterns (e.g., biomarker positive cells within a distance from the tumor/stroma interface), and, in general, have not been utilized for scoring patient samples in the context of guiding treatment decisions.

Currently, sophisticated quantification of the geographic distribution or pattern of cells within a tissue (e.g., modeling cell-to-cell interactions relative to random distributions, extraction of higher order statistics from density surface renderings, spatial assessment of autocorrelation between marker-positive cells, etc.) are not quantified nor utilized in a manner to guide a physician's determination of diagnosis, prediction of prognosis, or assessment of future treatments with a drug.

SUMMARY

In accordance with the embodiments herein, a method for visualizing a comparison between an experimental tissue sample and a reference tissue sample, selected from a database of reference samples is disclosed. The method described herein utilizes digital image analysis of an image of one or more tissue sections to then extract image analysis features from the tissue section to generate a dataset that associates a quantity of a specific analyte or biomolecule at a specific location in a tissue object in the tissue section. The numerical representation of the image of the tissue section is then compared to a reference database containing an assortment of tissue samples to determine which image analysis features are similar to those of a tissue sample within the reference database, and those that are different. These similarities and differences are then highlighted within a display of both images to facilitate a pathologist's analysis of the experimental tissue sample while seeing the similarities and differences within the image analysis features.

DETAILED DESCRIPTION OF EMBODIMENTS

In the following description, for purposes of explanation and not limitation, details and descriptions are set forth in order to provide a thorough understanding of the present invention. However, it will be apparent to those skilled in the art that the present invention may be practiced in other embodiments that depart from these details and descriptions without departing from the spirit and scope of the invention.

For purpose of definition, a tissue object is one or more of a cell (e.g., immune cell), cell sub-compartment (e.g., nucleus, cytoplasm, membrane, organelle), cell neighborhood, tissue compartment (e.g., tumor, tumor microenvironment (TME), stroma, lymphoid follicle, healthy tissue), blood vessel, and lymphatic vessel. Tissue objects are visualized by histologic stains which highlight the presence and localization of the tissue object. Tissue objects can be identified directly by stains specifically applied to highlight that tissue object (e.g., hematoxylin to visualize nuclei, IHC stain for a protein specifically found in a muscle fiber membrane), indirectly by stains applied which non-specifically highlight the tissue compartment (e.g., DAB staining), or are biomarkers known to be localized to a specific tissue compartment (e.g., nuclear-expressed protein, carbohydrates only found in the cell membrane).

For the purpose of this disclosure, patient status includes diagnosis of disease state, disease severity, disease progression, and therapy efficacy. Other patient statuses are contemplated.

Figure 1:
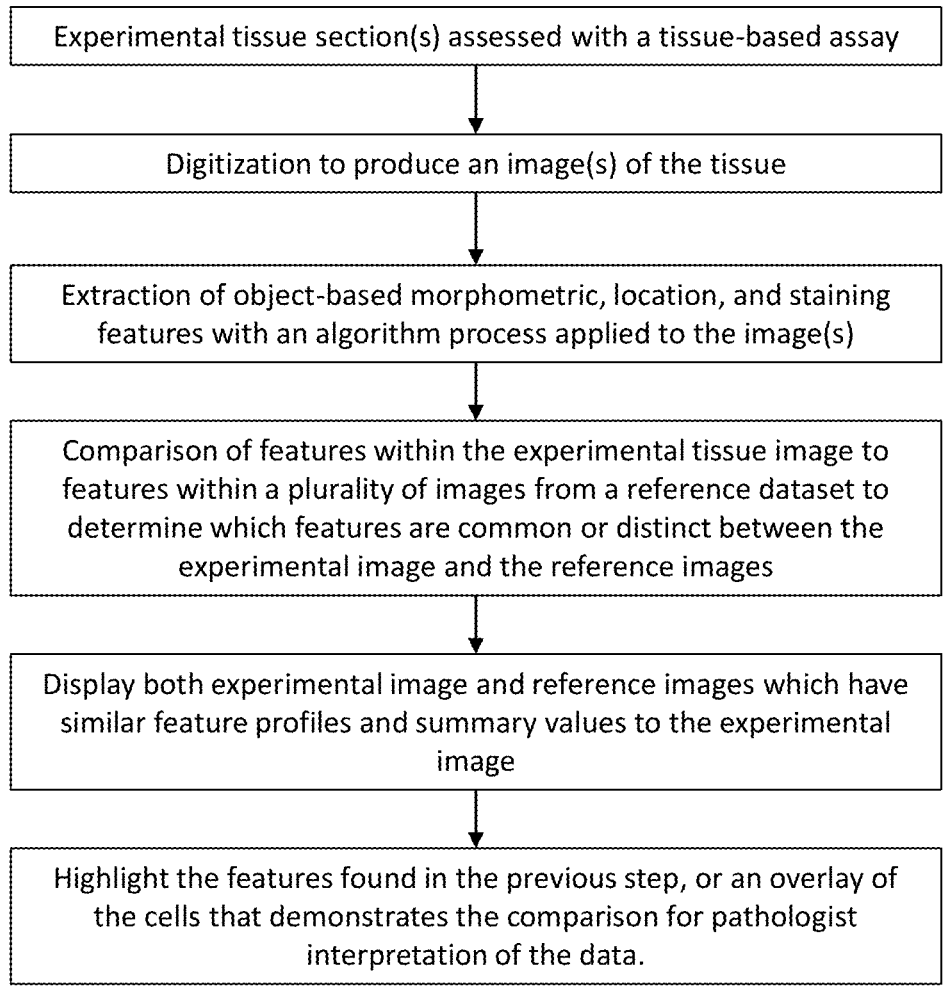
FIG. 1 provides an overview of a general method of the invention.

In one embodiment, as summarized in FIG. 1, the method may be used in the diagnostic setting to diagnose disease or direct therapy or the prognostic setting to predict patient outcome in relation to an expected course of disease. The method may be comprised of five steps: i) obtaining digital images of stained tissue sections; ii) applying a digital image analysis algorithm to the digital image to extract values for image analysis features which include morphometric features, localization features, and staining features of the tissue and tissue objects; iii) comparing the image analysis features and scoring endpoint(s) of the tissue section to a reference database consisting of comparative tissue sections iv) visually displaying the experimental image and at least one reference image in a manner in which both images are easily viewed; and v) highlighting image analysis features which are similar and/or different between the experimental and reference images. This embodiment can be also used in a patient selection setting, where a test is used to predict response to a specific therapeutic intervention.

In other embodiments, additional steps can be added to the previously disclosed method to allow for scoring of the stained tissue section. These additional steps include i) establishing a patient-specific score based on the extracted image analysis features; ii) comparing the patient-specific score to patient-specific scores in the reference database; iii) rank-ordering the tissue within the comparative reference database to establish a scoring interval for the patient specific-score; and iv) applying a patient selection criterion to the patient-specific score based on the rank order comparison.

In a further embodiment, the method may be applied to medical research for the purposes of understanding the nature of a disease or therapeutic intervention. The method may be comprised of six steps: i) obtaining digital images of stained tissue sections; ii) applying a digital image analysis algorithm to the digital image to extract values for image analysis features which include morphometric features, localization features, and staining features of the tissue and tissue objects; iii) deriving at least one scoring endpoint from the image analysis features; iv) comparing the image analysis features and scoring endpoint(s) of the tissue section to a reference database consisting of comparative tissue sections to determine a patient-specific score; v) comparing the patient-specific score to data from an associated biomarker, disease status, or outcome information from the patient pertaining to the tissue section in the reference database; vi) visually displaying the experimental image and at least one reference image in a manner in which both images are easily viewed; and vii) highlighting image analysis features which are similar and/or different between the experimental and reference images in order to highlight a relevant biological endpoint, such as the evaluation of pharmacodynamic effects or phenotypical differences. This embodiment can be used in a medical research setting, where a test is used to understand the mechanism of action for a disease or therapy.

A tissue-based assays enable evaluation of tissue objects and marker stains (e.g., presence and amount) for biologic molecules (e.g., chromatin, biomarkers) relative to position (e.g., x-y coordinates, polar coordinates) in the tissue. Tissue sample images are created and stored in computer memory or in a database for future recall and analysis using methods common to digital pathology.

Figure 2:
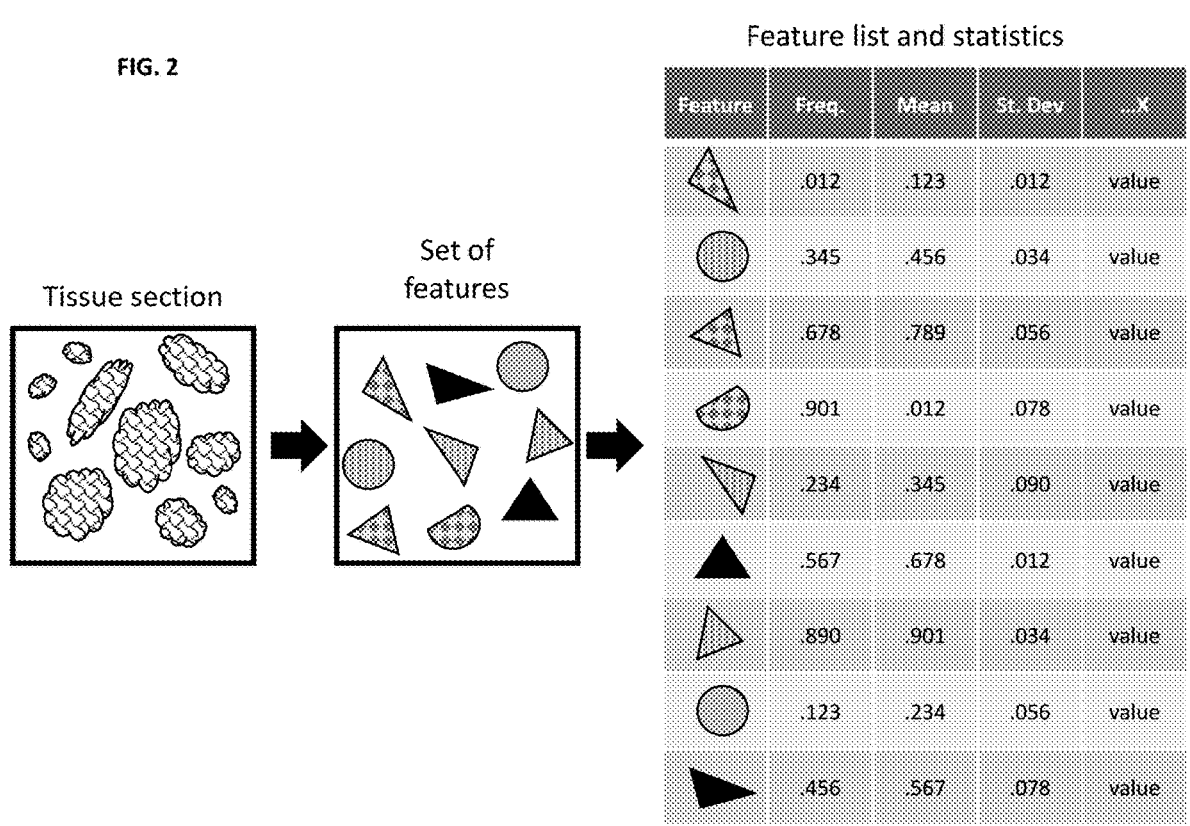
FIG. 2 illustrates the extraction of image analysis features and their transformation into a dataset.

In an embodiment of this invention, a digital tissue image analysis algorithm implemented by a computer is applied to each image of a patient specimen assayed with a tissue-based test to extract the morphometric, staining, and location features pertaining to tissue objects. The image analysis features are extracted for tissue objects. These features are then transformed into a numerical dataset representing the features, as seen in FIG. 2

Morphometric features are features related to the size, shape, area, texture, organization, and organizational relationship of tissue objects observed in a digital image. For example, and not limitation, morphometric features could be the area of a cell nucleus, the completeness of biomarker staining in a cell membrane, the diameter of a cell nucleus, the roundness of a blood vessel, lacunarity of biomarker staining in a nucleus, etc.

Staining features are features related to stain appearance, stain intensity, stain completeness, stain shape, stain texture, stain area, and stain distribution of specified IHC, ISH, and IF stains or dyes or amount of a molecule determined by MSI-based methodologies. Staining features are evaluated relative to tissue objects (e.g., average staining intensity in each cell in an image, staining level in a cell membrane, biomolecule expression in a nucleus).

Localization features are features related to position of a feature in the tissue section, spatial relationships of tissue objects relative to each other, relationship of image analysis features between tissue objects in the tissue section, and distribution of image analysis features within a tissue object. Location can be determined based on an absolute (x and y location based on pixel dimensions of image, μm from center of image defined by pixel dimensions of image) or relative (e.g., x and y position of cells relative to a tissue feature of interest such as a vessel, polar coordinates referenced to the center of mass of a tumor nest) coordinate system (e.g., x-y-z coordinates, polar coordinates). Location for specific image objects can be defined as the centroid of the object or any position enclosed by the object extending from the centroid to the exterior limits of the object.

Figure 3:
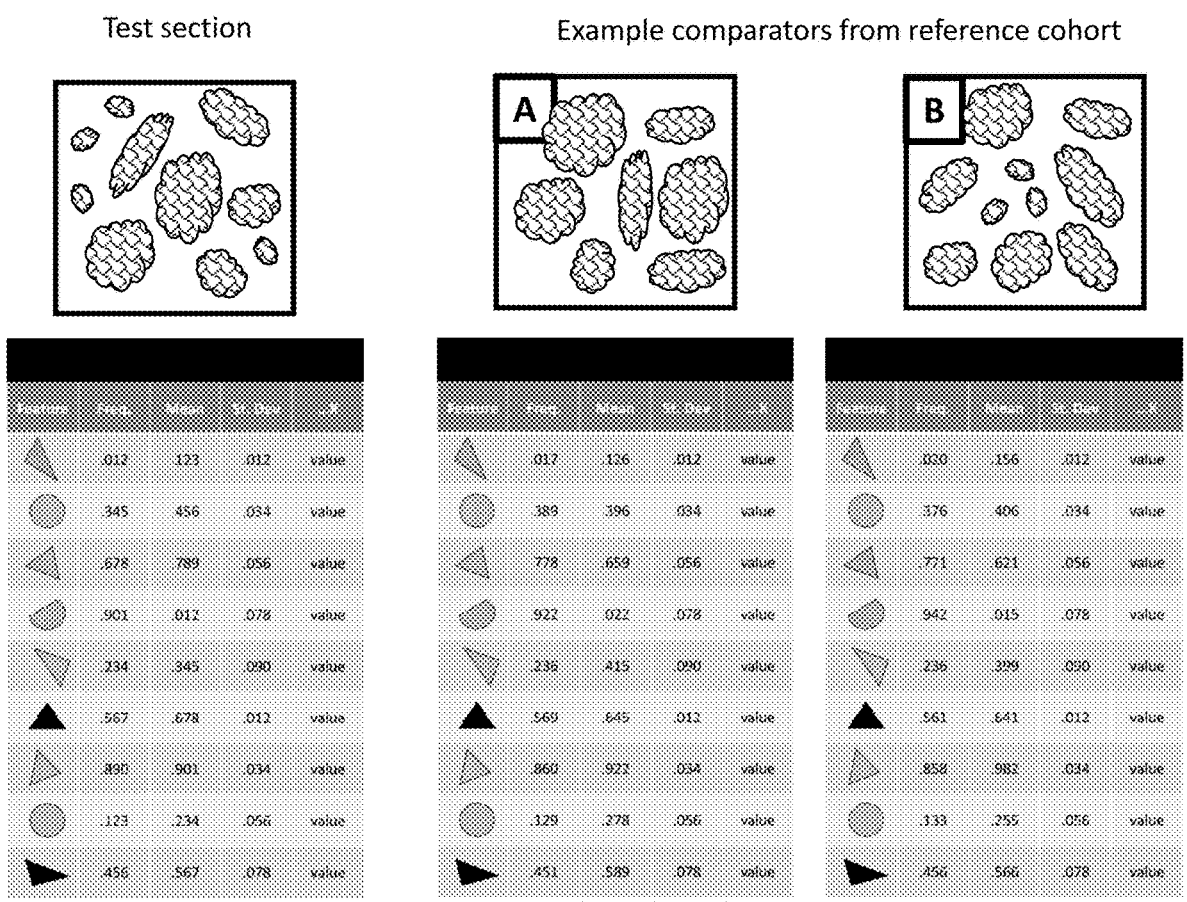
FIG. 3 illustrates an embodiment where relevant image analysis features are compared to image analysis features from the reference database.
Figure 4:
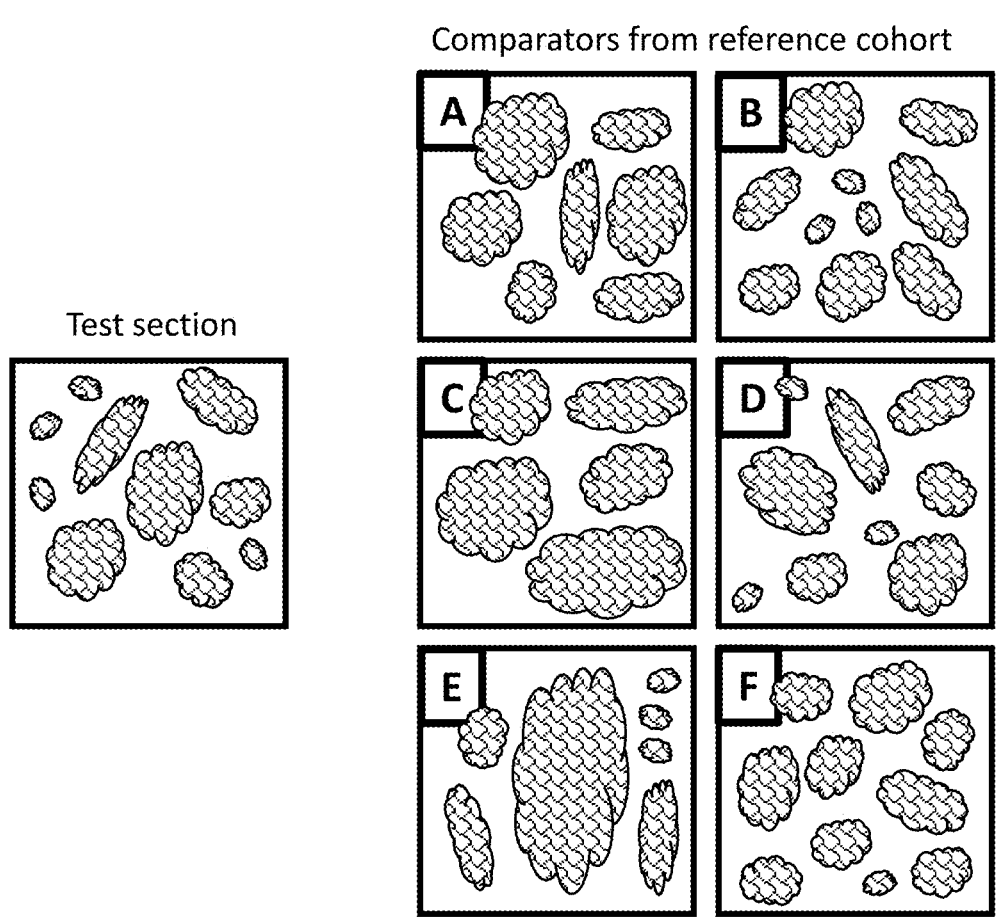
FIG. 4 illustrates an embodiment where relevant image analysis features are compared to images from the reference database.

In a further embodiment, the numerical dataset representing the features is compared to other numerical datasets that represent reference images within the reference database, as seen in FIG. 3. These comparisons can then be displayed to a pathologist, as seen in FIG. 4.

Figure 5:
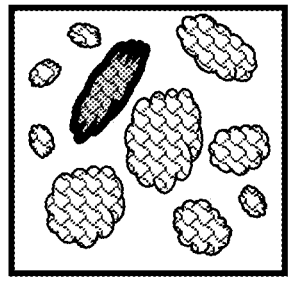
FIG. 5 illustrates an embodiment of the overlay used to visualize the similarities and differences between the experimental tissue section and the reference database.
Figure 5:
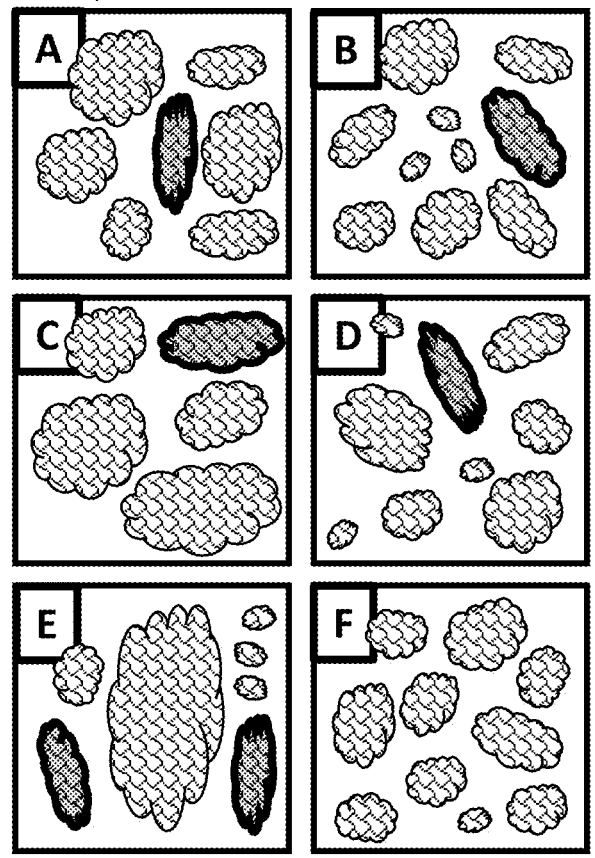
Figure 6:
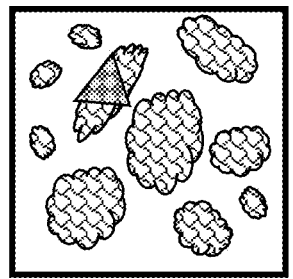
FIG. 6 illustrates another embodiment of the overlay used to visualize the similarities and differences between the experimental tissue section and the reference database.
Figure 6:
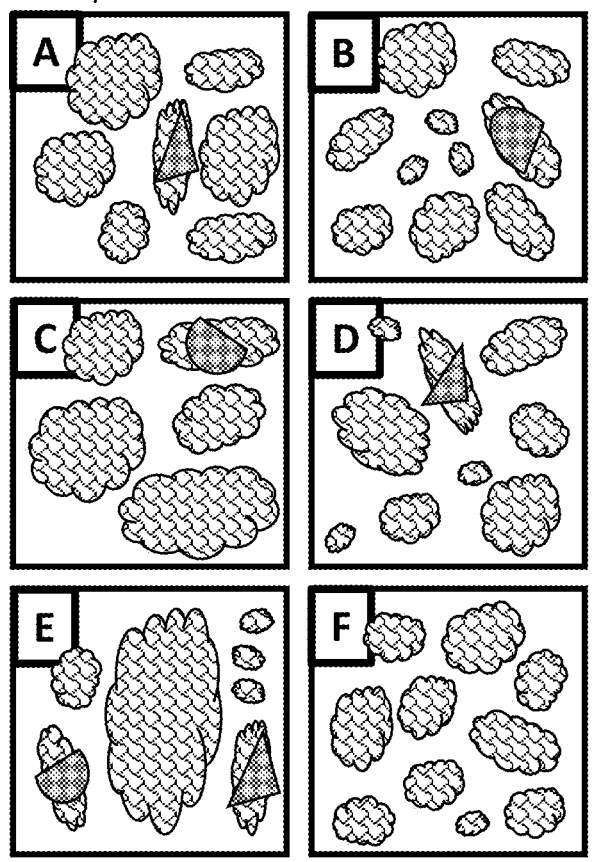
Figure 7:
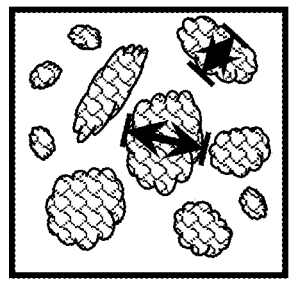
FIG. 7 illustrates a third embodiment of the overlay used to visualize the similarities and differences between the experimental tissue section and the reference database.
Figure 7:
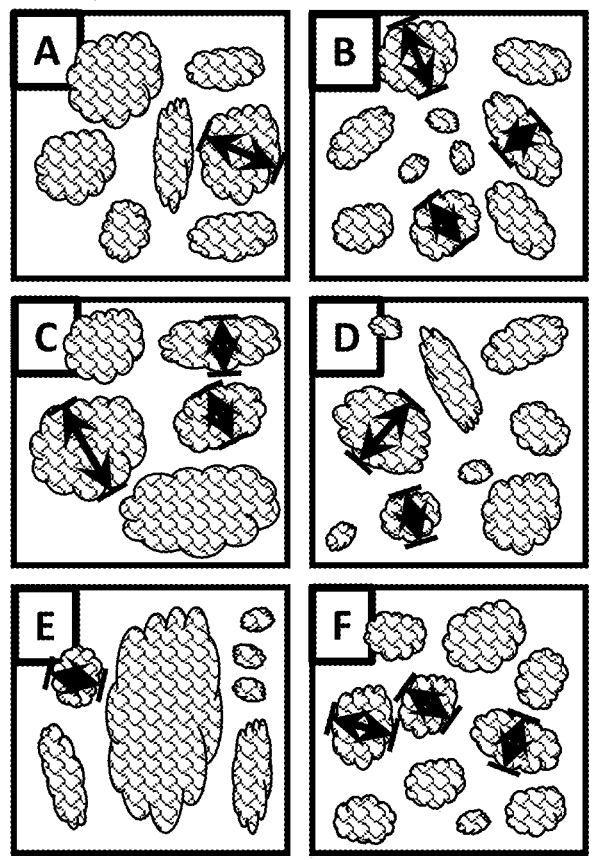

In another embodiment of the invention, the compared features between the experimental image and the reference image(s) are highlighted. The features can be highlighted by coloration overlay, shape or hatch or crosshatch overlay, arc or arrow overlay, or any number of other contemplated notations. FIGS. 5-7 each show examples related to this highlighting.

In other embodiments of the invention, the reference database includes outcome data for some or all of the patients associated with the reference samples. This patient outcome data allows for the pathologist reviewing the experimental image to compare the experimental image with known patient outcomes when making a predictive assessment of prognosis or therapy efficacy. This outcome data may be treatment efficacy, disease progression, or other medically relevant outcomes.

What is claimed is:

1. A method comprising:
  acquiring at least one experimental digital image of at least one stained tissue section;
  extracting at least one experimental image analysis feature from at least one tissue object in the at least one experimental digital image of at least one stained tissue section, to generate an experimental dataset of image analysis features;
  comparing the at least one experimental dataset to a reference dataset to determine commonalties and differences between the experimental dataset and the reference dataset, wherein the reference dataset contains a plurality of reference digital images of tissue sections which have at least one reference image analysis feature for each tissue section;
  displaying at least one reference digital image and the experimental digital image on a display device; wherein the at least one reference digital image contains at least one reference image analysis feature similar to, and different from, the at least one experimental image analysis feature; and displaying an overlay on top of the at least one reference and at least one experimental digital images to highlight the reference and experimental image analysis features in such a way to allow for a trained pathologist to interpret the comparison of image analysis features between the reference and experimental digital images.

2. The method of claim 1, wherein the image analysis features are selected from the group consisting of morphometric features, localization features, and staining features.

3. The method of claim 2, wherein the morphometric features are selected from the group consisting of size, shape, area, texture, organization, and organizational relationship.

4. The method of claim 2, wherein the staining features are selected from the group consisting of stain appearance, stain intensity, stain completeness, stain shape, stain texture, stain area, and stain distribution.

5. The method of claim 2, wherein the localization features are selected from the group consisting of position of a feature in the tissue section, the spatial relationships of tissue objects relative to each other, relationship of image analysis features between different tissue objects in the tissue section, and distribution of image analysis features within a tissue object.

6. The method of claim 1, further comprising:
using the overlain display, calculating a patient-specific score for stained tissue section which uses the similarities and differences of the experimental dataset with the reference dataset; and determining at least one patient status for a patient from whom the stained tissue section was acquired based on the patient-specific score.

7. The method of claim 6, wherein the at least one patient status is selected from the group consisting of diagnosis, disease severity, disease progression, and therapy efficacy.

8. The method of claim 1, wherein the reference dataset contains patient outcome data.

9. The method of claim 8, further comprising using the patient outcome data within the reference dataset to determine an experimental patient outcome for a patient from whom the stained tissue sample was acquired.

* * * * *